United States Patent [19]

Pittet et al.

[11] Patent Number: 4,515,967

[45] Date of Patent: May 7, 1985

[54] METHYL(METHYLTHIOALKYL)-1,3-DITHIOLANES

[75] Inventors: Alan O. Pittet, Atlantic Highlands; Thomas F. Courtney, Jr., Oakhurst; Ranya Muralidhara, Fair Haven, all of N.J.

[73] Assignee: International Flavors & Fragrances Inc., New York, N.Y.

[21] Appl. No.: 533,748

[22] Filed: Sep. 19, 1983

[51] Int. Cl.$^3$ ............................................. C07D 339/06
[52] U.S. Cl. ............................................ 549/39; 549/30
[58] Field of Search ................................... 549/39, 30

[56] References Cited

U.S. PATENT DOCUMENTS 3,904,556  9/1975  Pittet et al. ................... 252/522
4,101,307  6/1978  Clapot et al. ................... 549/30
4,153,442  5/1979  Clapot et al. ................... 549/30
4,224,051  9/1980  Clapot et al. ................... 549/30

OTHER PUBLICATIONS

Fischer et al, C.A., vol. 96, 20080m, p. 452, 1982.

Kim et al, Tetra. Letters, vol. 22, No. 42, pp. 4159–4162, 1981.

Zanno et al, "Syn. & Aroma Properties of Bis 1,1 & 2,2 (methylthio)", Perfumer Flavorist, vol. 7, Apr./May, pp. 48–50, 1982.

Primary Examiner—Henry R. Jiles
Assistant Examiner—J. G. Mullins
Attorney, Agent, or Firm—Arthur L. Liberman

[57] ABSTRACT

Described is the genus of methyl(methylthioalkyl)-1,3-dithiolanes defined according to the structure:

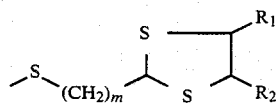

wherein $R_1$ and $R_2$ are the same or different and each represents methyl or hydrogen with the proviso that at least one of $R_1$ and $R_2$ is methyl; and wherein m represents an integer of 1 or 2 and uses of such methyl(methylthioalkyl)-1,3-dithiolanes in augmenting or enhancing the aroma or taste of foodstuffs.

4 Claims, 10 Drawing Figures

FIG.2 GLC PROFILE FOR FRACTION 2 OF EXAMPLE II.

FIG.1 GLC PROFILE FOR EXAMPLE I. CRUDE

FIG. 3 NMR SPECTRUM FOR EXAMPLE I.

FIG. 4
GLC PROFILE FOR EXAMPLE II. CRUDE

FIG. 5
GLC PROFILE FOR FRACTION 2 OF EXAMPLE II.

FIG. 6
NMR SPECTRUM FOR EXAMPLE II.

FIG. 9

GLC PROFILE FOR FRACTION 2 OF EXAMPLE IV.

FIG. 7

GLC PROFILE FOR FRACTION 3 OF EXAMPLE III.

FIG. 8 NMR SPECTRUM FOR EXAMPLE III.

FIG. 10 NMR SPECTRUM FOR EXAMPLE IV.

METHYL(METHYLTHIOALKYL)-1,3-DITHIOLANES

BACKGROUND OF THE INVENTION

This invention provides methyl(methylthioalkyl)-1,3-dithiolanes defined according to the generic structure:

wherein $R_1$ and $R_2$ are the same or different and each represents methyl or hydrogen with the proviso that at least one of $R_1$ and $R_2$ is methyl; and wherein m represents an integer of 1 or 2 and uses thereof in augmenting or enhancing the aroma or taste of foodstuffs.

Artificial flavoring agents for foodstuffs have received increasing attention in recent years. In many areas, such food flavoring agents are preferred over natural flavoring agents at least in part because of the uniform flavor that may be so obtained. For example, natural food flavoring agents such as extracts, essences, concentrates and the like are often subject to wide variation due to changes in the quality, type and treatment of the raw materials. Such variation can be reflected in the end product and results in unreliable flavor characterists and uncertainty as to consumer acceptance and cost. Additionally, the presence of the natural product in the ultimate food may be undesirable because of increased tendency to spoil. This is particularly troublesome in convenience and snack food usage where such products as dips, soups, chips, prepared dinners, canned foods, sauces, gravies and the like are apt to be stored by the consumer for some time prior to use.

The fundamental problem in preparing artifical flavoring agents is that of achieving as nearly as possible a true flavor reproduction. This generally proves to be a difficult task since the mechanism for flavoring development in many foods is not understood. This is notable in products having meaty, hydrolyzed, vegetable protein-like, sweet, meat extract-like, mushroom-like, turkey-like, chicken-like, pork-like and butterscotch aroma profiles and oniony, onion/roasted-like, hydrolyzed vegetable protein-like, sweet, meaty, meat extract-like, bready, mushroom-like, turkey-like, chicken-like, pork-like and butterscotch-like taste nuances.

Reproduction of meaty, hydrolyzed, vegetable protein-like, sweet, meat extract-like, mushroom-like, turkey-like, chicken-like, pork-like and butterscotch aroma nuances and oniony, onion/roasted, hydrolyzed vegetable protein-like, sweet, meaty, meat extract-like, mushroom-like, turkey-like, chicken-like, pork-like, butterscotch-like and bready taste nuances has been the subject of a long and continuous search by those engaged in the production of foodstuffs. The severe shortage of foods, especially protein foods, in many parts of the world has given rise to the need for utilizing non-meat sources of proteins and making such protein as palatable and as meat-like as possible. Hence, materials which will closely simulate or exactly reproduce the flavor and aroma of mushroom, hydrolyzed vegetable protein, beef broth, pot roast, onion and turkey are required. Furthermore, meat flavors have been enhanced previously by the use of such materials as monosodium glutamate. In many diets monosodium is not desired. Therefore, a need has arisen for a monosodium glutamate replacer.

Moreover, there are a great many meat containing or meat based foods presently distributed in a preserved form. Examples being condensed soups, dry-soup mixes, dry meat, freeze-dried or lyophilized meats, packaged gravies and the like. While these products contain meat or meat extracts, the fragrance, taste and other organoleptic factors are very often impaired by the processing operation and it is desirable to supplement or enhance the flavors of these preserved foods with versatile materials which have either roasted meat or sweet meat or vegetable-like or nut-like nuances.

Various 4-(methylthio)-butanal derivatives including 4-(methylthio)-butanal itself defined according to the structure:

and the diethyl acetal thereof are known for augmenting or enhancing the aroma or taste of foodstuffs and other consumable materials as is taught in U.S. Pat. No. 3,904,556 issued on Sept. 9, 1975 (the specification of which is incorporated by reference herein). Thus, the compound 4-(methylthio)-butanal diethyl acetal is taught in said U.S. Pat. No. 3,904,556 to provide a mushroom, heated onion flavor with green, sweet tomato, oniony and garlic nuances. The 4-(methylthio)-butanal itself is taught by said U.S. Pat. No. 3,904,556 to provide a mushroom-like, tomato-like, vegetable-like, cheesy and fruity taste.

Alkanes having 3-methylthio moieties are known in the prior art, for example, that disclosed in Chem.Abstracts, Volume 96:103327h having the structure:

This abstract is of Tetrahedron Letters, Volume 22, No. 42, pages 4159–4162, 1981, (Title: "THIOSULFONIUM IONS. METHYLTHIOLATION OF 3-METHYLTHIO-1-BUTENE AND CIS- AND TRANS-1-METHYLTHIO-2-BUTENE":Kim and Caserio).

Chem.Abstracts, Volume 96:20080m which is an abstract of Fischer, Liebigs Ann.Chem., 1981 (10), 1899–1902 discloses the compound having the structure:

wherein n is 2, 3 or 4 but does not disclose its organoleptic utilities.

Chem.Abstracts, Volume 84:164792v, (abstract of German Offenlegungsschrift No. 2,530,273) discloses the compound having the structure:

but does not disclose its organoleptic utilities.

U.S. Pat. No. 4,153,442 issued on May 8, 1979; U.S. Pat. No. 4,224,051 issued on Sept. 23, 1980; and U.S. Pat. No. 4,101,307 issued on June 18, 1978 each discloses plant growth regulating material compounds defined according to the generic structure:

in which

X and Y which may be the same or different and represent oxygen, sulphur or a radical N-B where B is hydrogen, a lower alkyl radical containing 1 to 4 carbon atoms, an optionally substituted aryl radical or an optionally substituted acyl radical containing from 1 to 4 carbon atoms, R and $R^1$ which may be the same or different and represent a lower alkyl radical containing from 1 to 4 carbon atoms or an acyl or amido radical containing from 1 to 4 carbon atoms; in addition, they may form with a cycle corresponding to the formula:

in which:

$R_1$, $R_2$, $R_3$ and $R_4$ which may be the same or different and represent hydrogen, an alkyl radical containing from 1 to 4 carbon atoms and optionally substituted by a halogen, the radicals $NO_2$, hydroxy, or alkoxy containing from 1 to 4 carbon atoms, A represents either a single bond or an alkylene chain containing from 1 to 4 carbon atoms optionally interrupted by an oxygen atom or a group N-B' where B' represents hydrogen, an optionally halogenated or hydroxylated alkyl group, an acyl group, the hydrocarbon portion of these radicals containing from 1 to 4 carbon atoms, or a cycle having in common with the preceding cycle 1 to 2 carbon atoms and containing from 3 to 6 carbon atoms, from 0 to 2 oxygen atoms and/or a group N-B, or a cycle corresponding to the formula Included in this generic structure is the genus defined according to the structure:

Although the generic structure set forth in the aforementioned U.S. Pat. Nos. 4,153,442, 4,224,051 and 4,101,307 contemplate within the genus a number of the compounds of the instant application, this disclosure is a "shot-gun" disclosure because it does not include the specific compounds of our invention, nor does it set forth the criticality of the compounds of our invention in their uses for their organoleptic properties.

Nagao, et al, Tetrahedron Letters No. 34, Pages 3167–3168 (1979) discloses the genus of compounds defined according to the structure:

in a synthetic route to yield certain ketones. In this genus R may be methyl, ethyl, propyl, butyl, tolyl, tolyl methoxy, allyl or phenyl. This genus is not part of the instant invention. Furthermore, the Nagao, et al paper does not disclose the organoleptic uses of such compounds.

Nothing in the prior art, however, discloses the compound having the structure:

wherein $R_1$ and $R_2$ are the same or different and each represents methyl or hydrogen with the proviso that at least one of $R_1$ and $R_2$ is methyl; and wherein m represents an integer of 1 or 2 or their organoleptic utilities.

BRIEF DESCRIPTION OF THE DRAWINGS

FIG. 2 is the GLC profile of Fraction 2 of the distillation product of the reaction product of Example I containing the compound having the structure:

(conditions: SE-30 column, 10'×0.125").

FIG. 3 is the NMR spectrum for the compound having the structure:

prepared according to Example I (conditions: Field strength: 100 MHz; Solvent: CFCl₃).

FIG. 4 is the GLC profile for the crude reaction product of Example II containing the compound having the structure:

(conditions: 10'×0.125", SE-30 column, programmed at 100°–220° C. at 8° C. per minute).

FIG. 6 is the NMR spectrum for the compound having the structure:

produced according to Example II (conditions: Field strength: 100 MHz; Solvent: CFCl₃).

FIG. 8 is the NMR spectrum for the compound having the structure:

produced according to Example III (conditions: Field strength: 100 MHz; Solvent: CFCl₃).

FIG. 10 is the NMR spectrum for the compound having the structure:

produced according to Example IV (conditions: Field strength: 100 MHz; Solvent: CFCl₃).

THE INVENTION

The present invention provides the novel methyl(methylthioalkyl)-1,3-dithiolanes useful for augmenting or enhancing the aroma or taste of foodstuffs, said methyl(methylthioalkyl)-1,3-dithiolanes being defined according to the structure:

wherein $R_1$ and $R_2$ are the same or different and each represents methyl or hydrogen with the proviso that at least one of $R_1$ and $R_2$ is methyl; and wherein m represents an integer of 1 or 2 and as well as methods for augmenting or enhancing or modifying the organoleptic properties, e.g., taste and aroma of said foodstuffs.

The methyl(methylthioalkyl)-1,3-dithiolanes of our invention augment or enhance meat, turkey, hydrolyzed vegetable-like protein, mushroom, bread-like, meat extract, beef broth, pot roast, onion and brothy flavored foodstuffs. The methyl(methylthioalkyl)-1,3-dithiolanes of our invention provide meaty, hydrolyzed vegetable protein-like, sweet, meat extract-like, mushroom-like, turkey-like, chicken-like, pork-like and butterscotch-like aroma nuances and oniony, onion/roasted, hydrolyzed vegetable protein-like, sweet, meaty, meat extract-like, bready, mushroom-like, turkey-like, chicken-like, pork-like and butterscotch-like taste nuances.

The methyl(methylthioalkyl)-1,3-dithiolanes of our invention defined according to the structure:

wherein $R_1$ and $R_2$ are the same or different and each represents methyl or hydrogen with the proviso that at least one of $R_1$ and $R_2$ is methyl; and wherein m represents an integer of 1 or 2 may be produced by means of reacting an $\alpha,\beta$-diol defined according to the structure:

wherein $R_1$ and $R_2$ are the same or different and each represents $C_1$–$C_3$ lower alkyl with a methylthioalkanal defined according to the structure:

where m is an integer of from 1 or 2 in the presence of a protonic acid catalyst such as para toluene sulfonic acid, xylene sulfonic acid, methane sulfonic acid, phosphoric acid and concentrated sulfuric acid. The reaction takes place in the presence of a solvent having a boiling point such that the reaction can proceed in a reasonable period of time, e.g., 1–12 hours at atmospheric pressure or pressures somewhat greater than atmospheric pressure (up to about 10 atmospheres). The reaction temperature may vary from between about 70° C. up to about 140° C. Reaction temperatures greater than 140° C. give rise to unnecessary breakdown of reaction product. Reaction temperatures lower than 70° C. give rise to too long a period of time of reaction. The solvents utilized must be inert to the reaction product as well as inert to the reactants. The solvent utilized must also have a boiling point of between 70° C. and 140° C. since the reaction is to take place under reflux conditions. The reaction solvent must also be capable of being completely removed from the product on distillation in view of the fact that the reaction products are used as food flavors for internal consumption. Accordingly, suitable solvents are, for example, cyclohexane, cyclopentane, cyclooctane, 1-methylcyclohexane, 1,2-dimethylcyclohexane, 1,2,4-trimethylcyclohexane, 2-ethyltetrahydrofuran, 2,5-dimethyltetrahydrofuran and the like.

Examples of the products of our invention and their organoleptic properties are as follows:

TABLE I

| Structure of Compound | Organoleptic Properties |
|---|---|
| | A meaty and hydrolyzed vegetable-like aroma with oniony, onion/roasted and hydrolyzed vegetable-like taste nuances at 0.1 ppm giving rise to usefulness in onion, hydrolyzed vegetable protein and brothy flavored foodstuffs. |

TABLE I-continued

| Structure of Compound | Organoleptic Properties |
|---|---|
| | A sweet, meaty, meat extract-like, hydrolyzed vegetable protein-like aroma profile with a sweet, meaty, meat extract-like, hydrolized vegetable protein-like and bready taste profile at 0.1 ppm giving rise to usefulness in meat extract, hydrolyzed vegetable protein, beef broth, bread and pot roast flavored foodstuffs. |
| | A mushroom-like and hydrolyzed vegetable protein-like aroma profile with a mushroom-like and hydrolyzed vegetable protein-like taste at 0.2 ppm giving rise to usefulness in mushroom, hydrolyzed vegetable protein and bread flavored foodstuffs. |
| | A meaty, hydrolyzed vegetable protein-like and meat extract-like aroma profile with a meaty, hydrolyzed vegetable protein-like and meat extract-like taste profile at 0.1 ppm. A turkey-like, chicken-like, pork-like and butterscotch-like aroma and taste profile at 1.0 ppm. This material is useful in meat, turkey and hydrolyzed vegetable protein flavored foodstuffs. It also provides an enhancement effect closely similar to that of monosodium glutamate and is therefor a monosodium glutamate replacer. |

At the end of the reaction as stated, supra, the reaction product is extracted from the reaction mass or the reaction mass is washed, for example, with saturated sodium chloride. The reaction product is then distilled preferably by means of vacuum distillation.

Thus, the methyl(methylthioalkyl)-1,3-dithiolanes produced according to our invention can be used to alter, vary, fortify, modify, enhance or otherwise improve the organoleptic properties, including flavor and/or aroma, of a wide variety of materials which are ingested, consumed, or otherwise organoleptically sensed.

The term "alter" in its various forms will be understood herein to mean the supplying or imparting a flavor character or note to an otherwise bland, relatively tasteless substance, or augmenting an existing flavor characteristic where the natural flavor is deficient in some regard, or supplementing the existing flavor or aroma impression to modify the organoleptic character. The materials which are so altered are generally referred to herein as consumable materials.

Such methyl(methylthioalkyl)-1,3-dithiolanes of our invention are accordingly useful in flavoring compositions. Flavoring compositions are hereintaken to mean those which contribute a part of the overall flavor impression by supplementing or fortifying a natural or artifical flavor in a material, as well as those which supply substantially all the flavor and/or aroma character to a consumable article.

The term "foodstuff" as used herein includes both solid and liquid ingestible materials for man or animals, which materials usually do, but need not, have nutritional value. Thus, foodstuffs includes meats, gravies, soups, convenience foods, malt and other alcoholic or non-alcoholic beverages, milk and dairy products, nut butters such as peanut butter and other spreads, seafoods including fish, crustaceans, mollusks and the like, candies, breakfast foods, baked goods, vegetables, cereals, soft drinks, snack foods, dog and cat foods, other veterinary products, and the like.

When the methyl(methylthioalkyl)-1,3-dithiolanes according to this invention are used in a food flavoring composition, they can be combined with conventional flavoring materials or adjuvants. Such co-ingredients or flavoring adjuvants are well known in the art for such use and have been extensively described in the literature. Apart from the requirement that any such adjuvant material is ingestibly acceptable, and thus non-toxic or otherwise non-deleterious, conventional materials can be used and broadly include other flavor materials, vehicles, stabilizers, thickeners, surface active agents, conditioners and flavor intensifiers.

Examples of preferred co-flavoring adjuvants are:
Methyl thiazole alcohol (4-methyl-5-beta-hydroxyethyl thiazole);
2-Methyl butanethiol;
4-Mercapto-2-butanone;
3-Mercapto-2-pentanone;
1-Mercapto-2-propanone;
Benzaldehyde;
Furfural;
Furfuryl alcohol;
2-Mercapto propionic acid;
Alkyl pyrazine;
Methyl pyrazine;
2-Ethyl-3-methyl pyrazine;
Tetramethyl pyrazine;
Polysulfides;
Dipropyl disulfide;
Methyl benzyl disulfide;
Alkyl thiophenes;
2-Butyl thiophene;
2,3-Dimethyl thiophene;
5-Methyl furfural;
2-Acetyl furan;
2,4-Decadienal;
Guiacol;
Phenyl acetaldehyde;
δ-Decalactone;
d-Limonene;
Acetoin;
Amyl acetate;
Maltol;
Ethyl butyrate;
Levulinic acid;
Piperonal;
Ethyl acetate;
n-Octanal;
n-Pentanal;
n-Hexanal;
Diacetyl;
Monosodium glutamate;
Monopotassium glutamate;
Sulfur-containing amino acids, e.g., Cysteine;
Hydrolyzed vegetable protein;
2-Methylfuran-3-thiol;
2-Methyldihydrofuran-3-thiol;
2,5-dimethylfuran-3-thiol;
Hydrolyzed fish protein; and
Tetramethyl pyrazine.

The methyl(methylthioalkyl)-1,3-dithiolanes or the compositions incorporating them, as mentioned above, can be combined with one or more vehicles or carriers for adding them to the particular product. Vehicles can be edible or otherwise suitable materials such as ethyl alcohol, propylene glycol, water and the like. Carriers include materials such as gum arabic, carrageenan, other gums and the like. The methyl(methylthioalkyl)-1,3-dithiolanes according to this invention can be incorporated with the carriers by conventional means such as spray-drying, drum-drying and the like. Such carriers can also include materials for coacervating the methyl(methylthioalkyl)-1,3-dithiolanes (and other flavoring ingredients, as present) to provide encapsulated products. When the carrier is an emulsion the flavoring composition can also contain emulsifiers such as mono- and diglycerides or fatty acids and the like. With these carriers or vehicles, the desired physical form of the composition can be prepared.

The quantity of methyl(methylthioalkyl)-1,3-dithiolanes utilized should be sufficient to impart the desired flavor characteristic to the product, but on the other hand, the use of an excessive amount of the derivative is not only wasteful and uneconomical, but in some instances too large a quantity may unbalance the flavor or other organoleptic properties of the product consumed. The quantity used will vary depending upon the ultimate foodstuff; the amount and type of flavor initially present in the foodstuff; the further process or treatment steps to which the foodstuff will be subjected; regional and other preference factors; the type of storage; if any, to which the product will be subject; and the preconsumption treatment, such as baking, frying, and so on, given to the product by the ultimate consumer. Accordingly, the terminology "effect amount" and "sufficient amount" is understood in the context of the present invention to be quantitatively adequate to alter the flavor of the foodstuff.

It is accordingly preferred that the ultimate composition contain from about 0.001 parts per million (ppm) to about 250 ppm of methyl(methylthioalkyl)-1,3-dithiolanes or mixtures thereof. More particularly, in food compositions it is desirable to use from about 0.001 ppm to 100 ppm for enhancing flavors and in certain preferred embodiments of the invention, from about 0.001 to 50 ppm of the derivatives are included to add positive flavors to the finished product.

The amount of methyl(methylthioalkyl)-1,3-dithiolanes or mixtures thereof of our invention to be utilized in flavoring compositions can be varied over a wide range depending upon the particular quality to be added to the foodstuff. Thus, amounts of one or more derivatives according to the present invention of from about 0.05 ppm up to 80 or 90 percent of the total flavoring composition can be incorporated in such compositions. It is generally found to be desirable to include from about 0.05 ppm to about 0.1 percent of the methyl(methylthioalkyl)-1,3-dithiolanes in such compositions.

The following examples are given to illustrate embodiment of the invention as it is preferred to practice it. It will be understood that these examples are illustrative and the invention is not to be considered as restrictive thereto except as indicated in the appended claims.

All parts, proportions, percentages, and ratios here are by weight unless otherwise indicated.

EXAMPLE I

PREPARATION OF 4-METHYL-2-(METHYLTHIOMETHYL)-1,3-DITHIOLANE

Reaction:

Into a 100 ml reaction flask equipped with reflux condensor, heating mantle, hot plate equipped with magnetic stirring apparatus and magnetic stirring bar is placed 10 ml cyclohexane, 0.5 grams of para toluene sulfonic acid and 10.8 grams (0.1 mole) of 1,2-propanedithiol. Over a period of one hour, 9 grams (0.1 mole) of methylthioacetaldehyde is added to the reaction mass. The reaction mass is then heated to reflux and maintained at reflux for a period of eight hours. At the end of the eight hour period the reaction mass is transferred to a separatory funnel and washed with one 50 ml portion of a saturated aqueous sodium chloride solution, then dried over anhydrous sodium sulfate, filtered and distilled. The distillation takes place on a micro vigreux column yielding the following fractions:

| Fraction No. | Vapor Temp. (°C.) | Liquid Temp. (°C.) | Vacuum mm/Hg. Pressure |
|---|---|---|---|
| 1 | 85/ | 104/ | 1:0 |
| 2 | 100 | 116 | 1:0 |
| 3 | 94 | 118 | 1:0 |
| 4 | 65 | 140 | 1:0 |

Figure 1:
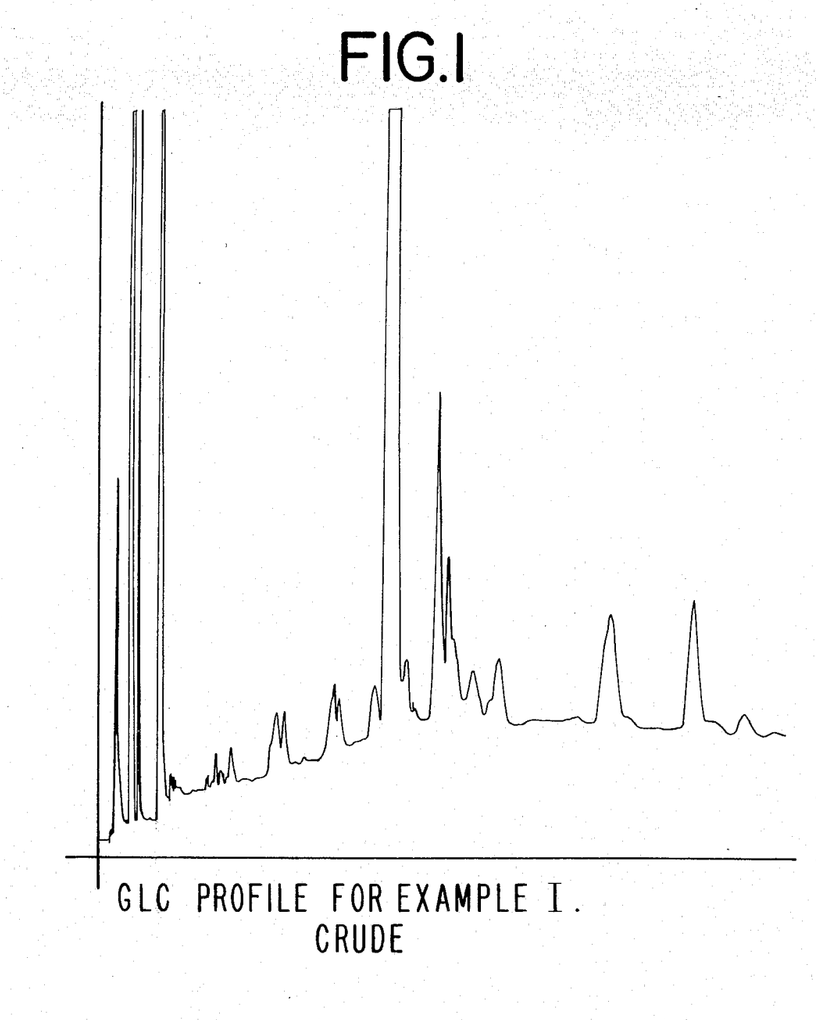
FIG. 1 is the GLC profile of the crude reaction product of Example I containing the compound having the structure.

FIG. 1 is the GLC profile for the crude reaction product prior to distillation.

Figure 2:
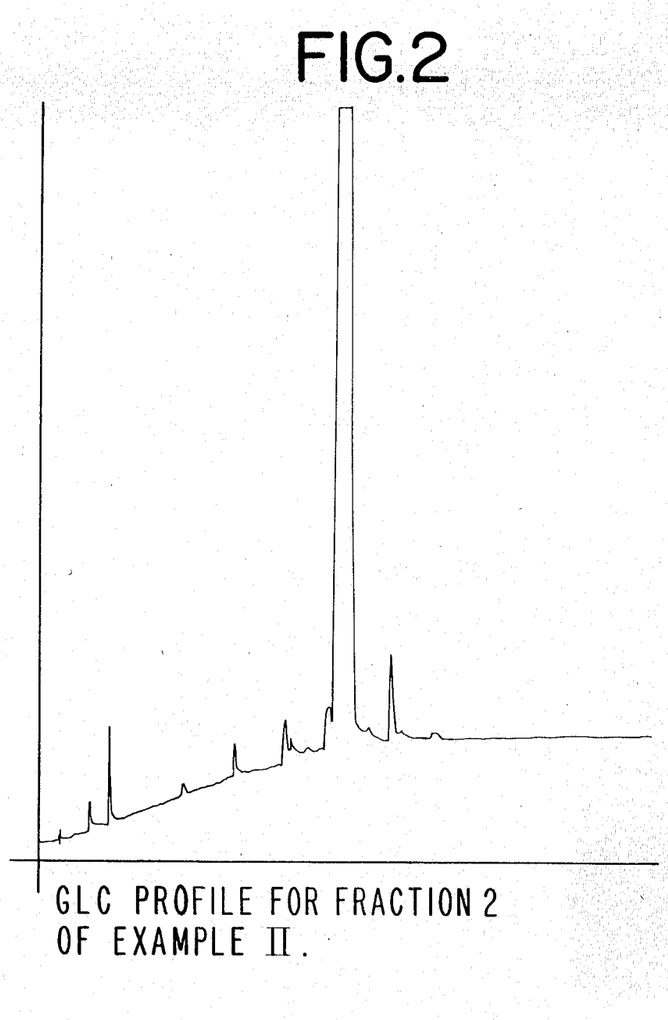

FIG. 2 is the GLC profile for Fraction 2 of the foregoing distillation (SE-30 column ... 10'×0.125").

Figure 3:
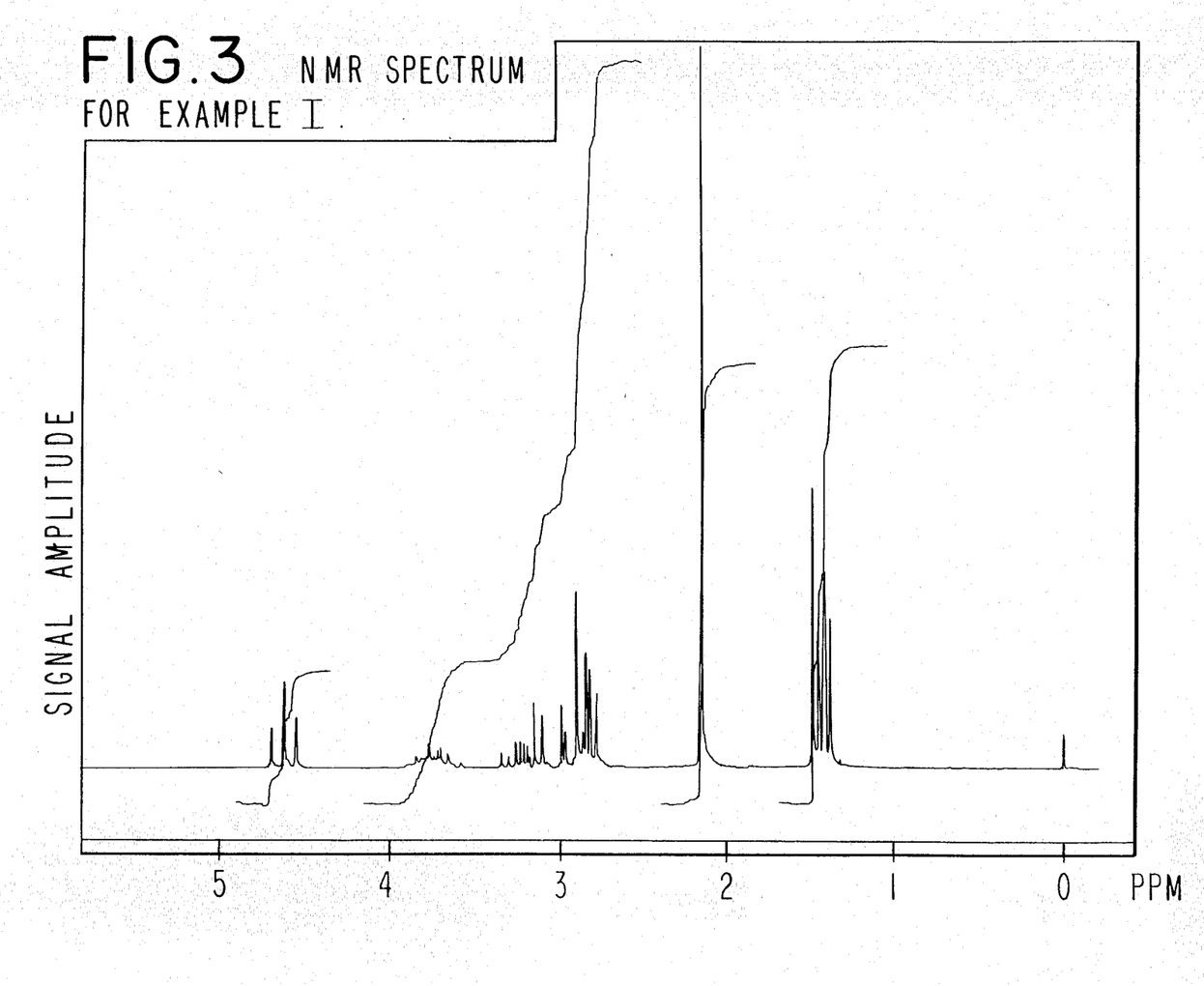

FIG. 3 is the NMR spectrum for the compound having the structure:

(Conditions: Field strength: 100 MHz; Solvent: CFCl₃).

EXAMPLE II

PREPARATION OF 4,5-DIMETHYL-2-(METHYLTHIOMETHYL)-1,3-DITHIOLANE

Reaction:

Into a 100 ml reaction flask equipped with reflux condensor, heating mantle and hot plate with magnetic stirring apparatus and stirring bar is placed 10 ml cyclohexane, 0.5 grams of para toluene sulfonic acid and 12 grams (0.1 mole) of 2,3-butanedithiol. Over a period of seven hours, 9 grams (0.1 mole) of methylthioacetaldehyde is added to the reaction mass. The reaction mass is then heated to reflux while collecting water of reaction and refluxed for a period of seven hours. The reaction mass is then transferred to a separatory funnel and washed with one 50 ml portion of saturated sodium chloride solution, dried over anhydrous sodium sulfate, filtered and distilled on a micro vigreux column yielding the following fractions:

| Fraction No. | Vapor Temp. (°C.) | Liquid Temp. (°C.) | Vacuum mm/Hg. Pressure (gms) |
|---|---|---|---|
| 1 | 108/ | 125/ | 1.0 |
| 2 | 115 | 127 | 1.0 |
| 3 | 116 | 128 | 1.0 |
| 4 | 116 | 132 | 1.0 |
| 5 | 114 | 150 | 1.0 |

Figure 4:
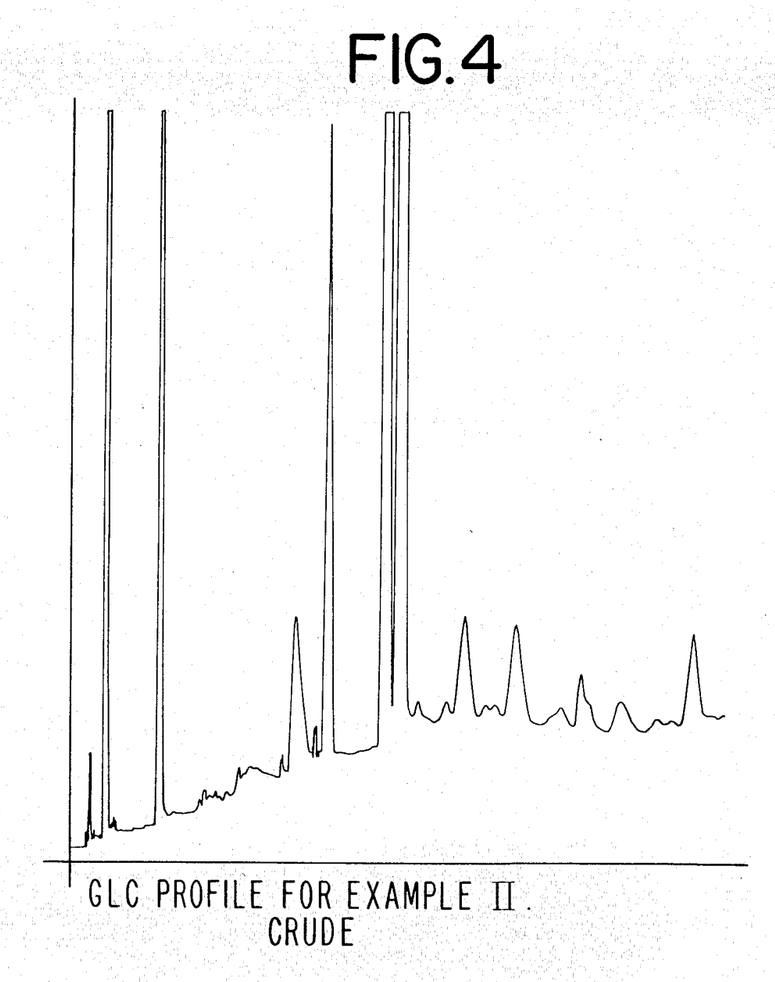

FIG. 4 is the GLC profile for the crude reaction product (conditions: 10'×0.125", SE-30 column, programmed at 100°-220° C. at 8° C. per minute).

Figure 5:
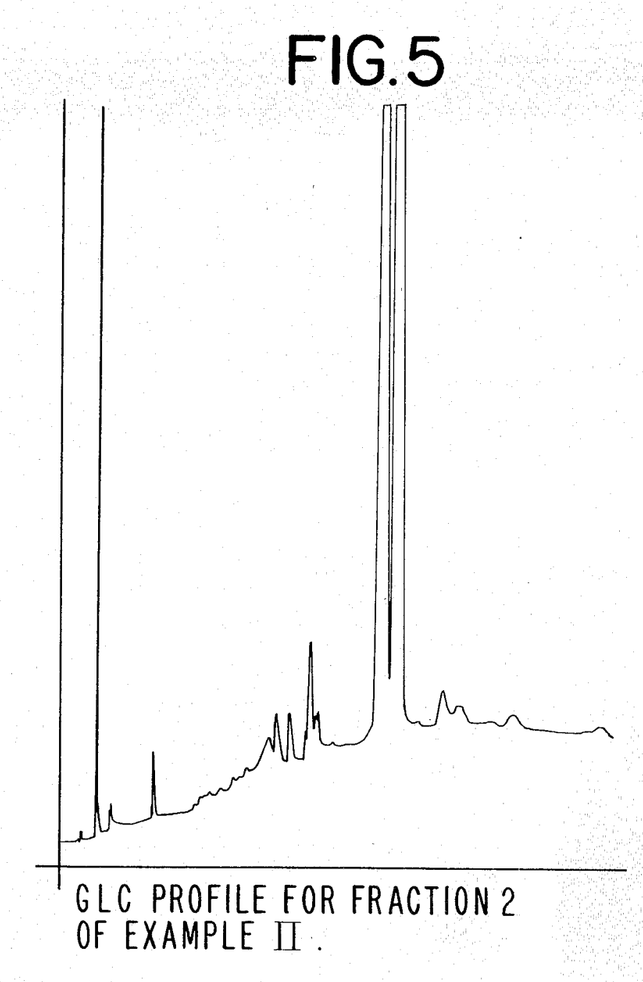
FIG. 5 is the GLC profile for Fraction 2 of the distillation product of the reaction product of Example II containing the compound having the structure.

FIG. 5 is the GLC profile for Fraction 2 of the foregoing distillation.

Figure 6:
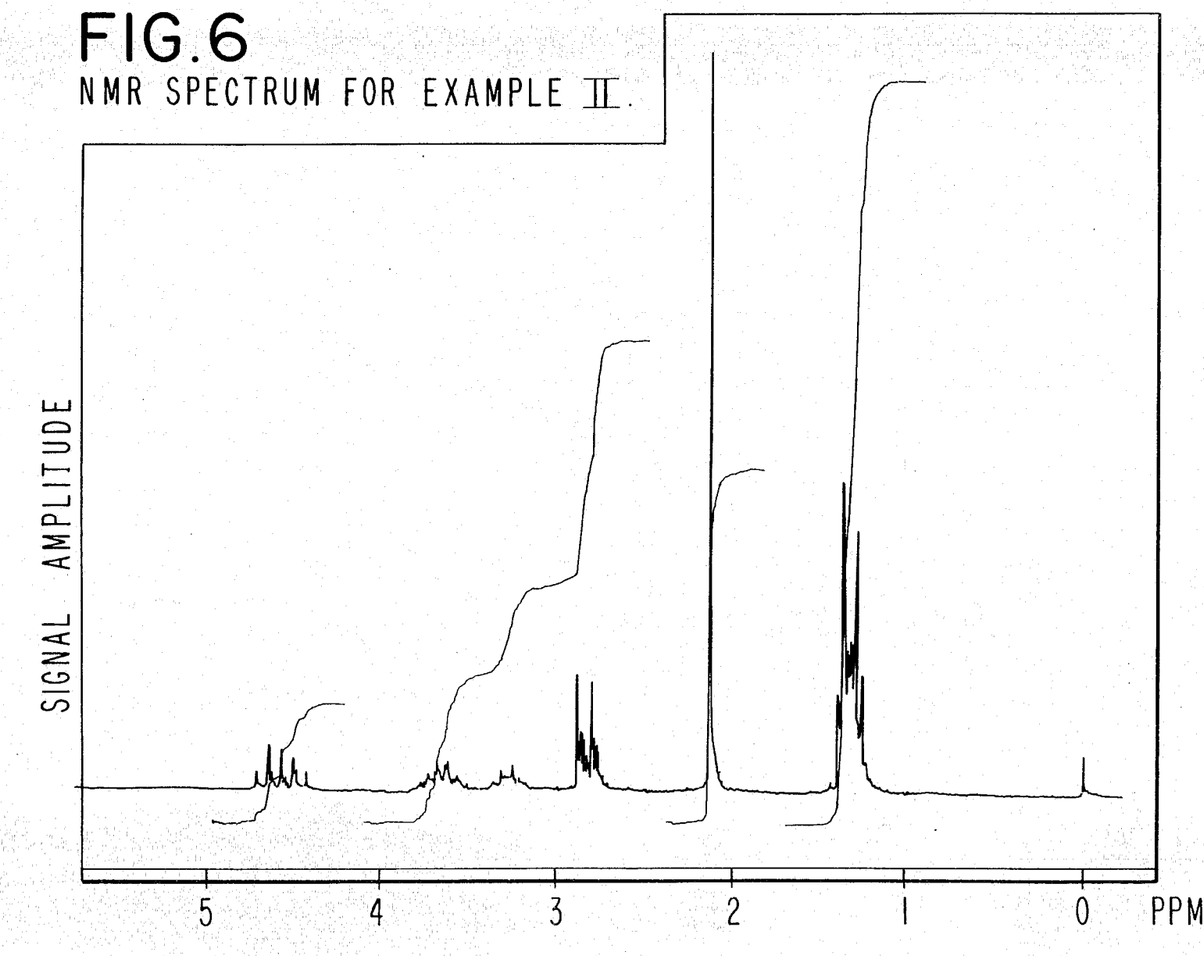

FIG. 6 is the NMR spectrum for the compound having the structure:

(conditions: Field strength: 100 MHz; Solvent: CFCl₃).

EXAMPLE III

PREPARATION OF 4-METHYL-2-[2-(METHYLTHIO)-ETHYL]-1,3-DITHIOLANE

Reaction:

Into a 100 ml reaction flask equipped with reflux condensor, heating mantle and hot plate with magnetic stirring apparatus and stirring bar is placed 10 ml cyclohexane, 0.5 grams para toluene sulfonic acid and 11 grams (0.1 mole) of 1,2-propanedithiol. Over a period of two hours, 10.4 grams (0.1 mole) of methional is added to the reaction mass. The reaction mass is then heated to reflux and maintained at reflux collecting water of reaction over a period of nine hours. The reaction mass is then transferred to a separatory funnel and washed with one 50 ml portion of a saturated aqueous sodium chloride solution and then dried over anhydrous sodium sulfate, filtered and distilled on a micro vigreux column yielding the following fractions:

| Fraction No. | Vapor Temp. (°C.) | Liquid Temp. (°C.) | Vacuum mm/Hg. Pressure (gms) |
|---|---|---|---|
| | 126/ | 137/ | 1.0 |
| 2 | 130 | 144 | 1.0 |
| 3 | 131 | 145 | 1.0 |
| 4 | 125 | 160 | 1.0 |

Figure 7:
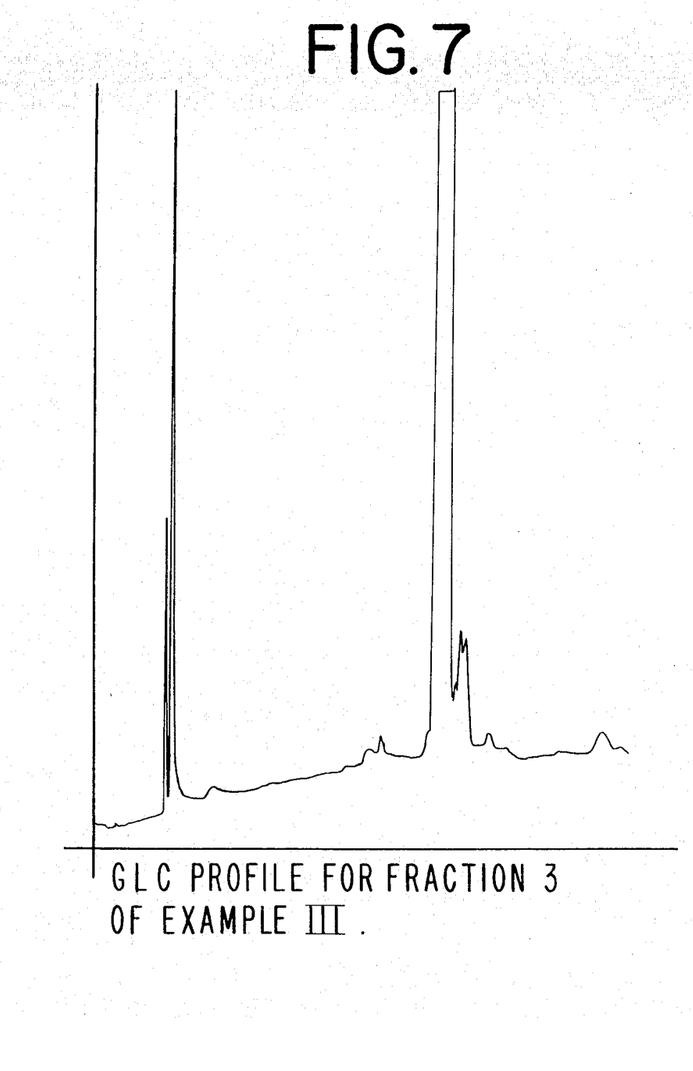
FIG. 7 is the GLC profile for Fraction 3 of the distillation product of the reaction product of Example III containing the compound having the structure.

FIG. 7 is the GLC profile for Fraction 3 of the foregoing distillation.

Figure 8:
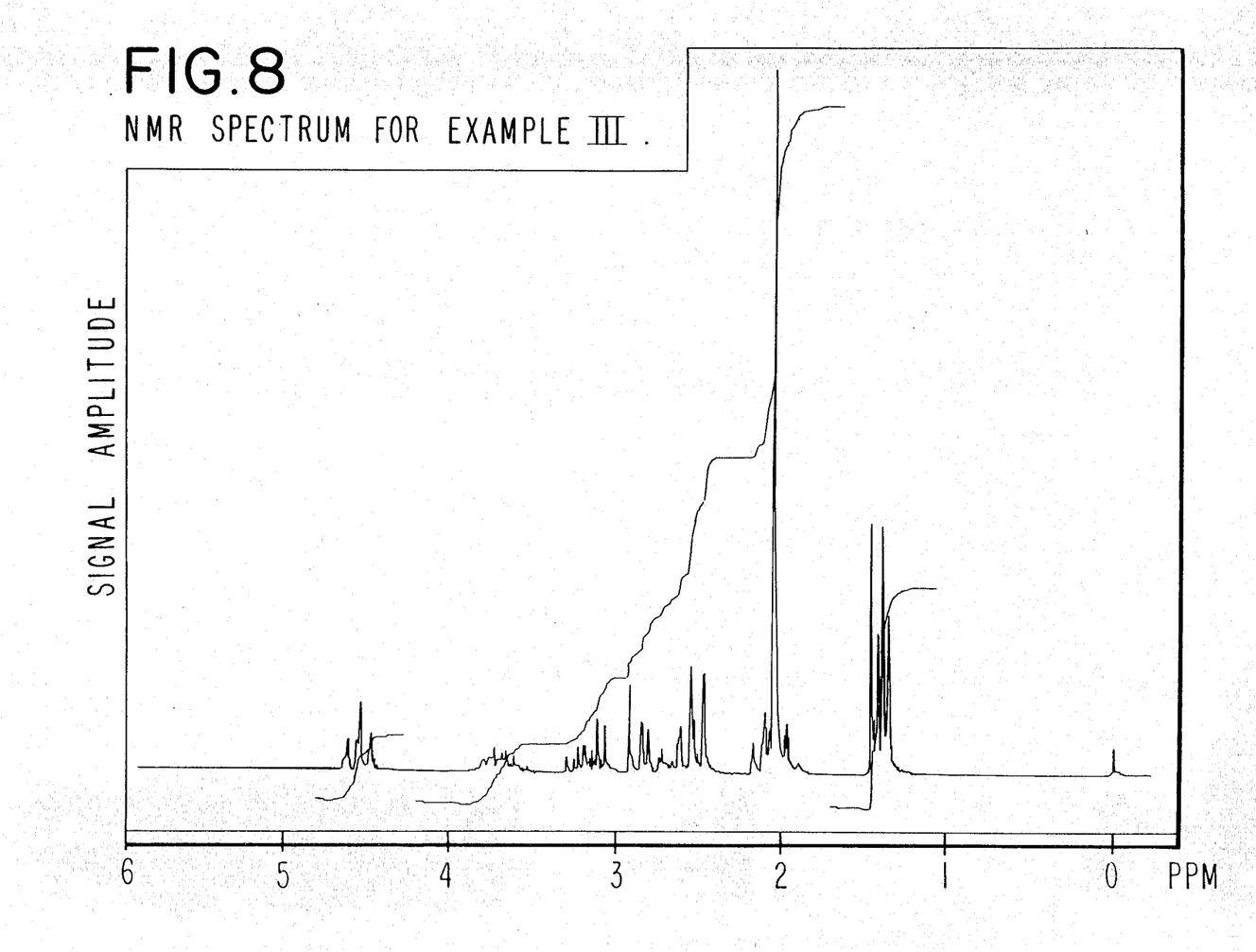

FIG. 8 is the NMR spectrum for the compound having the structure:

(Conditions: Field strength: 100 MHz; Solvent; CFCl₃).

EXAMPLE IV

PREPARATION OF 4,5-DIMETHYL-2-[2-(METHYLTHIO)ETHYL]-1,3-DITHIOLANE

Reaction:

Into a 100 ml reaction flask equipped with reflux condensor, heating mantle and hot plate with magnetic stirring apparatus and stirring bar is placed 10 ml cyclohexane, 0.5 grams para toluene sulfonic acid and 13 grams (0.1 mole) of 2,3-butanedithiol. Over a period of one hour, with stirring is added 10.4 grams (0.1 mole) of methional. The reaction mass is then refluxed over a period of 7.5 hours while collecting water of formation. The reaction mass is then cooled and transferred to a separatory funnel and washed with one 50 ml portion of saturated aqueous sodium chloride and then dried over anhydrous sodium sulfate, filtered and distilled on a micro vigreux column yielding the following fractions:

| Fraction No. | Vapor Temp. (°C.) | Liquid Temp. (°C.) | Vacuum mm/Hg. Pressure (gms) |
|---|---|---|---|
| 1 | 109/ | 133/ | 1.0 |
| 2 | 117 | 138 | 1.0 |
| 3 | 118 | 139 | 1.0 |
| 4 | 86 | 160 | 1.0 |

Figure 9:
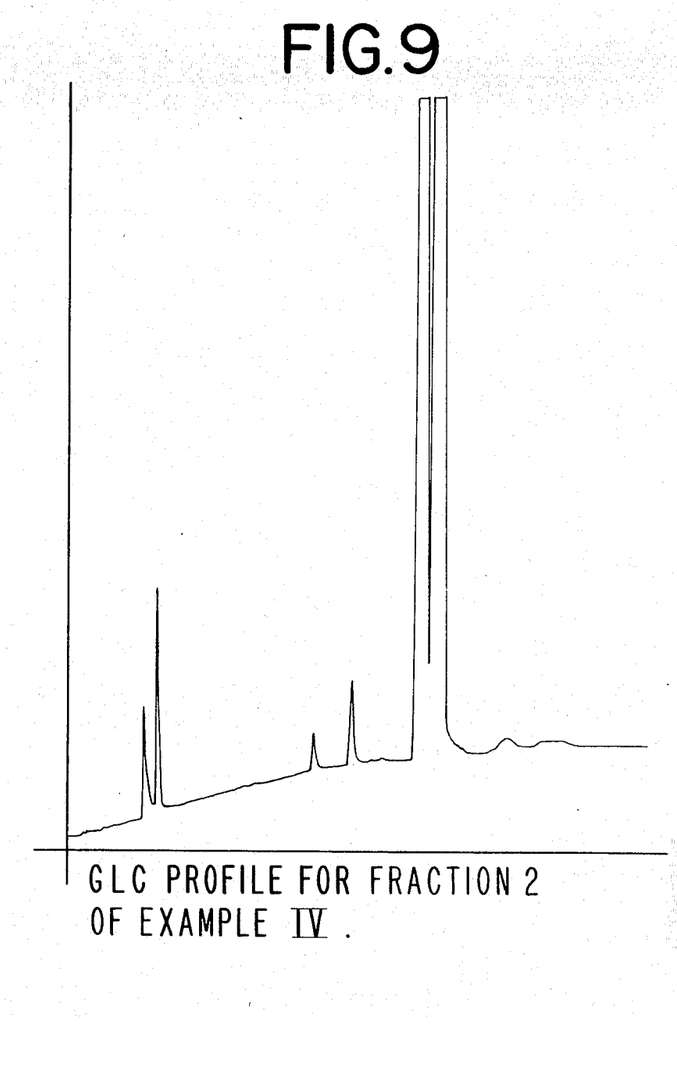
FIG. 9 is the GLC profile for Fraction 2 of the distillation product of the reaction product of Example IV containing the compound having the structure.

FIG. 9 is the GLC profile for Fraction 2 of the foregoing distillation.

Figure 10:
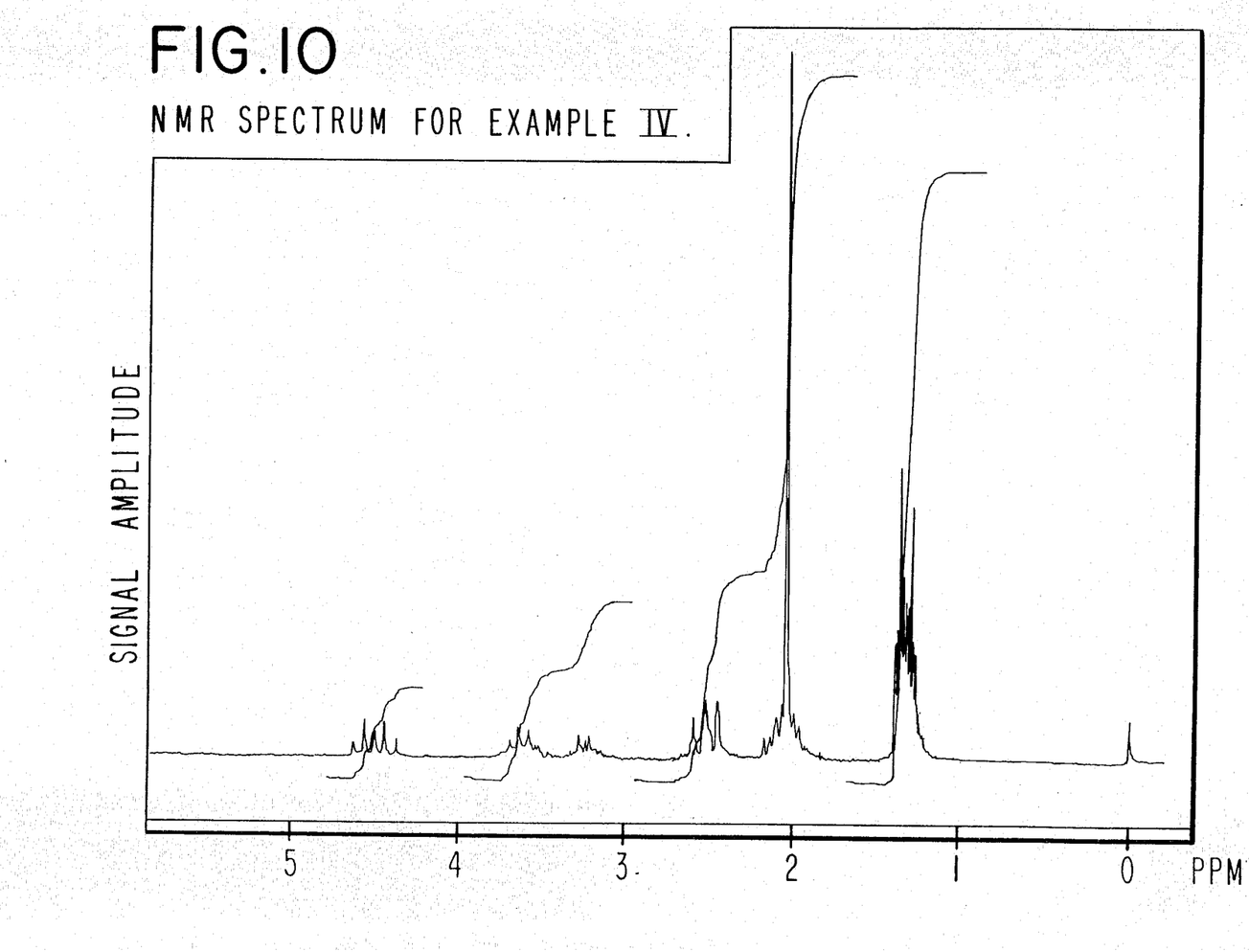

FIG. 10 is the NMR spectrum for the compound having the structure:

prepared according to this example (conditions: Field strength: 100 MHz; Solvent: CFCl₃).

EXAMPLE V

The compound having the structure:

prepared according to Example I is dissolved in propylene glycol to provide a 0.1% solution. The solution in the amount of 0.9 grams is added to 7.3 grams of a soup base consisting of:

| Ingredient | Parts by Weight |
|---|---|
| Fine ground sodium chloride | 35.5 |
| Hydrolyzed vegetable protein | 27.5 |
| Monosodium glutamate | 18.0 |
| Sucrose | 11.0 |
| Beef fat | 5.5 |
| Sethness caramel color (powder B & C). | 2.7 |

The resulting mixture has an oniony hydrolyzed vegetable protein-like beef broth-like aroma and flavor.

EXAMPLE VI

The compound having the structure:

produced according to Example II is added to a 2% solution of Wyler's "Beef Flavored Instant Bouillon" (manufactured by Wyler Foods, Division of Borden, Inc., Chicago, Ill., U.S.A.).

(Ingredients: salt, hydrolyzed vegetable protein, malto dextrin, sugar beef fat, water, monosodium glutamate, flavorings, corn sugar, beef extract, caramel color, hydrogenated vegetable fat and U.S. certified food color)
at the rate of 0.1 ppm. The resulting beef flavor has a sweet, meaty, meat extract-like and hydrolyzed vegetable protein-like aroma profile with a sweet, meaty, meat extract-like, hydrolyzed vegetable protein-like and bready taste profile.

EXAMPLE VII

A meat gravy is prepared containing 0.2 ppm by weight of the compound having the structure:

prepared according to Example III using a beef base and beef fat. The resulting beef gravy containing the compound having the structure:

is then added to mushrooms cooked using boiling water at a rate of 10 parts gravy to 100 parts cooked mushrooms. The resulting mushroom platter has an excellent natural-like beefy, savoury mushroom flavor with bready nuances.

When the compound having the structure:

is added to this platter at the level of 0.1 ppm, an intense meaty note is created . . . 50% more intense than without the compound having the structure:

The compound having the structure:

acts as a replacer for monosodium glutamate.

EXAMPLE VII

GRAVY FLAVOR

A gravy flavoring material is prepared by admixing the following ingredients:

| Ingredients | Parts by Weight |
| --- | --- |
| Diacetyl (5% solution in propylene glycol) | 0.20 |
| Furfural | 0.20 |
| 2-Acetyl-3-ethyl pyrazine | 1.0 |
| 2-Methyl-2-isobutyl thiazole | 0.05 |
| Methional | 2.0 |
| 2,5-Dimethyl-3-furyl thioacetate | 0.8 |

A bench panel of five individuals compared the above formulation with one containing the compound having the structure:

which is added at the rate of 0.005 parts by weight.

The flavor with the compound having the structure:

has a turkey-like, chicken-like, pork-like and butterscotch nuances.

When the compound having the structure:

is added at the rate of 1.0 ppm to a standard chicken frankfurter containing 50 parts by weight chicken and 50 parts by weight port, the chicken nuances are intensified 50% greater than without the compound having the structure:

This intensification shows that the compound having the structure:

is a replacer for monosodium glutamate.

What is claimed is:

1. A compound defined according to the structure:

wherein $R_1$ and $R_2$ are the same or different and each represents methyl or hydrogen with a proviso that at least one of $R_1$ and $R_2$ is methyl; and wherein m represents an integer of 1 or 2 and with the further proviso that when m is 1, then both $R_1$ and $R_2$ are methyl.

2. The compound of claim 1 having the structure:

3. The compound of claim 1 having the structure:

4. The compound of claim 1 having the structure:

* * * * *